United States Patent
Goia et al.

(10) Patent No.: US 12,396,960 B2
(45) Date of Patent: Aug. 26, 2025

(54) STABLE DISPERSIONS OF SILVER NANOPARTICLES AND METHODS OF PREPARATION THEREOF

(71) Applicant: NOBEL /NOBLE ELEMENTS/ LLC, Cheyenne, WY (US)

(72) Inventors: Dan Goia, Flemington, NJ (US); Ajeet Kumar, Piscataway, NJ (US)

(73) Assignee: NOBEL/Noble Elements/LLC, Cheyenne, WY (US)

( * ) Notice: Subject to any disclaimer, the term of this patent is extended or adjusted under 35 U.S.C. 154(b) by 57 days.

(21) Appl. No.: 17/544,228

(22) Filed: Dec. 7, 2021

(65) Prior Publication Data

US 2022/0175685 A1    Jun. 9, 2022

Related U.S. Application Data

(60) Provisional application No. 63/122,379, filed on Dec. 7, 2020.

(51) Int. Cl.
*A61K 9/51* (2006.01)
*C09D 11/38* (2014.01)

(52) U.S. Cl.
CPC ............ *A61K 9/5115* (2013.01); *C09D 11/38* (2013.01)

(58) Field of Classification Search
None
See application file for complete search history.

(56) References Cited

U.S. PATENT DOCUMENTS

| 5,957,828 A * | 9/1999 | Hayashi ............ B22F 9/24 516/97 |
|---|---|---|
| 2009/0214766 A1 | 8/2009 | Magdassi et al. |
| 2018/0207728 A1 | 7/2018 | Teramoto et al. |
| 2020/0086318 A1 | 3/2020 | Bilgin et al. |

FOREIGN PATENT DOCUMENTS

| DE | 69718578 T2 | 11/2003 |
| EP | 2045028 A1 | 4/2009 |
| JP | 4697008 B2 | 6/2011 |

OTHER PUBLICATIONS

PubChem, Compound Summary Pyrogallol (Year: 2023).*
Kumar et al., Cytotoxicity of phloroglucinol engineered silver (Ag) nanoparticles against MCF-7 breast cancer cell lines, Materials Chemistry and Physics 220 (2018) 402-408 (Year: 2018).*
Nishimura et al., Role of base in the formation of silver nanoparticles synthesized using sodium acrylate as a dual reducing and encapsulating agentw, Phys. Chem. Chem. Phys., 2011, 13, 9335-9343 (Year: 2011).*
Chakraborty et al., A comparative analysis of dialysis based separation methods for assessing copper oxide nanoparticle solubility, Environmental Nanotechnology, Monitoring & Management 12 (2019) 100258 (Year: 2019).*
Deleebeeck et al., Unified pH Measurements of Ethanol, Methanol, and Acetonitrile, and Their Mixtures withWaterSensors 2021, 21, 3935 (Year: 2021).*
International Search Report and Written Opinion received in corresponding International Application No. PCT/US2021/062193, mailed on Mar. 16, 2022, 15 pages.

* cited by examiner

*Primary Examiner* — Anna R Falkowitz
*Assistant Examiner* — Edwin Coleman Mitchell
(74) *Attorney, Agent, or Firm* — Rimon P.C.

(57) ABSTRACT

Disclosed herein are compositions comprising silver nanoparticles with uniform particles and a narrow particle size distribution. Also disclosed herein are processes for preparing and purifying the dispersions of silver nanoparticles.

6 Claims, 4 Drawing Sheets

STABLE DISPERSIONS OF SILVER NANOPARTICLES AND METHODS OF PREPARATION THEREOF

CROSS-REFERENCE TO RELATED APPLICATION

This application claims priority to U.S. patent application No. 63/122,379, filed on Dec. 7, 2020. These and all other extrinsic materials discussed herein, including publications, patent applications, and patents, are incorporated by reference in their entirety. Where a definition or use of a term in an incorporated reference is inconsistent or contrary to the definition of that term provided herein, the definition of that term provided herein applies and the definition of the term in the reference does not apply.

FIELD OF THE INVENTION

The field of the invention is stable dispersions of silver nanoparticles and methods of preparation thereof.

BACKGROUND

Silver nanoparticles have found many applications in biomedicine as well as various high technology fields such as electronics, catalysis, bio-imaging, solar cells, ink-jet printing, glass and ceramic staining, and spectroscopic research. Accordingly, a need exists for the development of preparation processes that yield concentrated and stable dispersions of uniform silver nanoparticles.

SUMMARY

In an aspect, provided herein is a composition, comprising a dispersion of uniform silver nanoparticles having a diameter of up to about 15 nm. In some embodiments, the nanoparticles have a diameter ranging from about 5 nm to about 15 nm. In some embodiments, the nanoparticles have a diameter ranging from about 9 nm to about 13 nm. In some embodiments, the nanoparticles have a diameter ranging from about 10 nm to about 12 nm.

In some embodiments, the dispersion comprises from about 1 wt % to about 5 wt % of silver nanoparticles. In some embodiments, the dispersion is concentrated to comprise up to about 60 wt % of silver nanoparticles. In some embodiments, the silver is elemental silver.

In an aspect, a composition comprising a dispersion of silver nanoparticles is provided, wherein at least 98%, at least 99%, or wherein each nanoparticle of the silver nanoparticles has a diameter of between 5-20 nm. In an aspect, a composition comprising a dispersion of silver nanoparticles is provided, wherein at least 98%, at least 99%, or wherein each nanoparticle of the silver nanoparticles has a diameter of less than 15 nm. It is contemplated that the compositions described herein can be storage stable for a period of at least two years, at least 18 months, at least 12 months, or at least 6 months at ambient temperature and pressure. The stability can be defined as lack of deposition of particles and change in the UV-Vis spectrum of the dispersion.

The silver nanoparticles can be free of any coatings. Additionally, or alternatively, the dispersion can comprise between 1-5 wt % of silver nanoparticles, which can optionally be concentrated to at least 40 wt %, at least 50 wt %, or at least 60 wt % silver nanoparticles. In some aspects, a difference between the minimum diameter and a maximum diameter of the silver nanoparticles does not exceed 10 nm. In some aspects, a difference between the minimum diameter and a maximum diameter of at least 90%, at least 95%, at least 98%, or at least 99% of the silver nanoparticles does not exceed 10 nm.

In an aspect, a nanoparticle composition comprising a population of silver nanoparticles and at least one dispersion medium is provided, wherein at least 98% of the nanoparticles have a diameter of less than 20 nm, or between 8-15 nm. In some embodiments, a difference between the minimum diameter and a maximum diameter of the silver nanoparticles does not exceed 15 nm. In some embodiments, a difference between the minimum diameter and a maximum diameter of at least 98% of the nanoparticles does not exceed 10 nm. In some embodiments, at least 98% of the nanoparticles have a diameter of less than 15 nm. In some embodiments, the silver nanoparticles and the at least one dispersion medium form a dispersion, and the dispersion comprises between 1-5 wt % of silver nanoparticles. In some embodiments, the dispersion is concentrated to comprise up to about 60 wt % of silver nanoparticles. In some embodiments, the composition composes an inkjet printing formulation. In some embodiments, the composition composes a drug delivery vector.

In some embodiments, the composition is stable for a period of at least about 12 months.

In some embodiments, the silver nanoparticles are free of polymeric coatings. In some embodiments, the silver nanoparticles are free of high molecular weight organic coatings.

In another aspect, provided herein is a composition, comprising a homogeneous solution of silver nitrate and a benzene triol.

In some embodiments, the composition further comprises at least one oxidation product of the benzene triol.

In some embodiments, the benzene triol is phloroglucinol.

In some embodiments, the composition is acidic.

In an aspect, provided herein is a process of preparing a composition comprising a dispersion of uniform silver nanoparticles, comprising contacting or reacting silver nitrate with a benzene triol at about 25° C. in the presence of a solvent to afford a homogeneous latent reaction mixture of benzene triol and silver ions.

In an aspect, a method of preparing a composition comprising a dispersion of silver nanoparticles is provided, comprising a step of contacting silver nitrate with a benzene triol at between 20-30 degrees Celsius in the presence of a solvent to form a mixture.

In some embodiments, the solvent is water.

In some embodiments, the solvent is a water and alcohol mixture where the alcohol is completely miscible with water. The alcohol may be a low molecular weight aliphatic one such as methanol, ethanol, propanol and its isomers.

In some embodiments, the benzene triol is phloroglucinol.

In some embodiments, the process or method further comprises monitoring the pH.

In some embodiments, the process or method is conducted under neutral or acidic conditions.

In some embodiments, the latent reaction mixture comprising a solution of silver nitrate and a benzene triol is vigorously agitated.

In some embodiments, the process or method is conducted in the absence of a dispersing agent. In some embodiments, the process does not comprise the thermal decomposition of silver(+1)-oxide species. In some embodiments, the process or method does not require heat. In some embodiments, the latent reaction mixture is free of a dispersing agent. In some embodiments, the process or method is carried out in the absence of polysaccharides.

In some embodiments, the reaction is quenched by the rapid addition of concentrated base to the reaction mixture.

In some embodiments, the base is sodium hydroxide.

In some embodiments, base is added until a pH of about 13 or greater is achieved.

In some embodiments, the quenching is achieved by adding concentrated base to the reaction mixture over a period of up to about 5 seconds.

In some embodiments, the quenching is achieved by adding concentrated base to the reaction mixture over a period of up to about 1 second.

In some embodiments, the concentration of the sodium hydroxide is about 0.05N to 10N.

In some embodiments, a bimolecular byproduct of phloroglucinol is formed.

In some embodiments, the aggregation of silver particles is prevented.

In some embodiments, the process or method does not comprise addition of an organic polymer.

In some embodiments, the process or method further comprises removing excess phloroglucinol and its oxidation byproducts by dialysis.

In some embodiments, the process or method further comprises the step of separating the silver particles from the mixture and optionally the step of drying the particles.

In some embodiments, the silver particles are separated by ultrafiltration.

In some embodiments, process or method does not comprise the addition of a colloid stabilizer.

In some embodiments, the process or method comprises contacting silver nitrate with a benzene triol at between 20-30 degrees Celsius in the presence of a solvent to form a mixture, vigorously agitating the mixture after the step of contacting, quenching the mixture by adding a concentrated base to the reaction mixture after the step of vigorously agitating, removing excess benzene triol and its oxidation byproducts from the mixture by dialysis, and separating the silver particles from the mixture.

In an aspect, provided herein is a process of preparing a composition comprising a dispersion of uniform silver nanoparticles, comprising contacting or reacting silver nitrate with a benzene triol at about 25° C. in the presence of a solvent to afford a homogeneous latent reaction mixture of benzene triol and silver ions, with the proviso that a dispersing agent is not used.

In an aspect, provided herein is a process of preparing a composition comprising a dispersion of uniform silver nanoparticles, comprising contacting or reacting silver nitrate with a benzene triol at about 25° C. in the presence of a solvent to afford a homogeneous latent reaction mixture of benzene triol and silver ions, with the proviso that a dispersing agent comprising polysaccharides is not used.

In an aspect, provided herein is a process of preparing a composition comprising a dispersion of uniform silver nanoparticles, comprising contacting or reacting silver nitrate with a benzene triol at about 25° C. in the presence of a solvent to afford a homogeneous latent reaction mixture of benzene triol and silver ions, with the proviso that the reaction is not carried out with heat.

In another aspect, provided herein is an inkjet printing formulation, comprising the silver nanoparticles as disclosed herein.

In another aspect, the dried inkjet printed deposit are electrically conductive at room temperature.

In another aspect, provided herein is a drug delivery vector, comprising the silver nanoparticles as disclosed herein. In some embodiments, the vector further comprises at least one therapeutic agent. In some embodiments, the vector further comprises at least one chemotherapeutic agent.

Other advantages and benefits of the disclosed compositions and methods will be apparent to one of ordinary skill with a review of the following drawings and detailed description

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Some of their useful properties manifest when silver nanoparticles are effectively dispersed in liquids as true "colloidal systems." Dilute stable dispersions of silver nanoparticles can be prepared in the absence of dispersing agents by adding a suitable reducing agent to a solution containing silver ions. At the low ionic strength of such systems, the range of the electrostatic repulsive forces between particles extends sufficiently far to effectively screen the attractive forces and prevent their aggregation. In concentrated systems, however, the high ionic strength reduces drastically the range of electrostatic forces and the particles aggregate due to the unscreened attractive Van der Waals forces. This undesired outcome is typically prevented by adding dispersing agents (usually macromolecular organic compounds) that provide sufficient spatial ('steric') separation between the nanoparticles to prevent their irreversible attachment. While effective, dispersants have a negative impact on the functional properties of particles in many applications.

Disclosed herein are processes to prepare highly concentrated dispersions of silver nanoparticles without using colloid stabilizers (i.e., dispersants). A merit of the disclosed precipitation process is in its ability to generate particles with a surface free of polymeric organic coatings. This offers the possibility to subsequently deposit onto their surface polymeric additives that address specific practical needs.

In inkjet printing, for example, the silver nanoparticles can be functionalized to tailor their wetting and sintering properties. The optoelectronic properties can be altered following the adsorption of various species/compounds with benefits in applications such as sensor plasmon resonance (SPR) sensing. In bio-medical applications the biocompatibility, bioavailability, and therapeutic action of silver nanoparticles can be altered by coating with various organic compounds. Additionally, in drug delivery 'therapeutic loads' can be tethered to the surface and carried to the intended targets in the body. Particularly, organic molecules such containing amino and disulfide functional groups (aminoacids, proteins) are suitable for this purpose. Other molecule containing functional groups with high affinity for the silver surface are potential candidates.

Disclosed herein are methods for precipitating highly concentrated stable dispersions of uniform silver nanoparticles in absence of dedicated dispersing agents. The precipitation process disclosed herein is carried out at ambient temperature and comprises or consists in adding sodium hydroxide into a solution containing silver nitrate and phloroglucinol. The latter is an organic compound from the benzenetriols family with the brut formula $C_6H_6O_3$. Its structure is shown (Formula (I).)

Phloroglucinol structure
(I)

Phloroglucinol can be viewed as a result of inserting a third hydroxyl group into the 'meta' position of resorcinol. Resorcinol, a benzenediol, has been used to reduce silver ions to metallic silver and form uniform silver particles, however the particles have diameters between 40 and 100 nm. Its 'para' isomer, hydroquinone was used to precipitate even larger (0.5 to 3.0 micrometer) silver spheres. As disclosed herein, phloroglucinol, a benzenetriol, can be used as well to precipitate highly dispersed uniform silver particles.

This disclosure describes the experimental conditions in which phloroglucinol generates at elevated volumetric metal concentration highly dispersed uniform silver particles. Conditions in which the reduction of silver ions and the nucleation of silver metallic phase proceeds very rapidly and uniformly in the entire reaction space are disclosed herein. As a result of the oxidation of di- and tri-hydroxyl substituted benzene, protons are released (see Equation 1), the reducing ability of phloroglucinol decreases with pH and it cannot reduce silver ions in neutral or acidic conditions.

$$C_6H_6O_3 \rightarrow C_6H_4O_3 + 2H^+ + 2e^-$$  Eq. 1

Since the pH of the silver nitrate solution is acidic, the resorcinol and silver ions can coexist in solution at ambient temperature forming a homogeneous latent reaction mixture. Once the pH of the system is rapidly increased, the electrons from the reductant molecules are transferred rapidly to silver ions in their vicinity to form silver atoms. This creates conditions for a rapid nucleation burst resulting in a very large number of nuclei. Since the fraction of silver atoms involved in the formation of nuclei is large, at the end of the subsequent growth phase the size of the final particles is still small.

Figure 1:
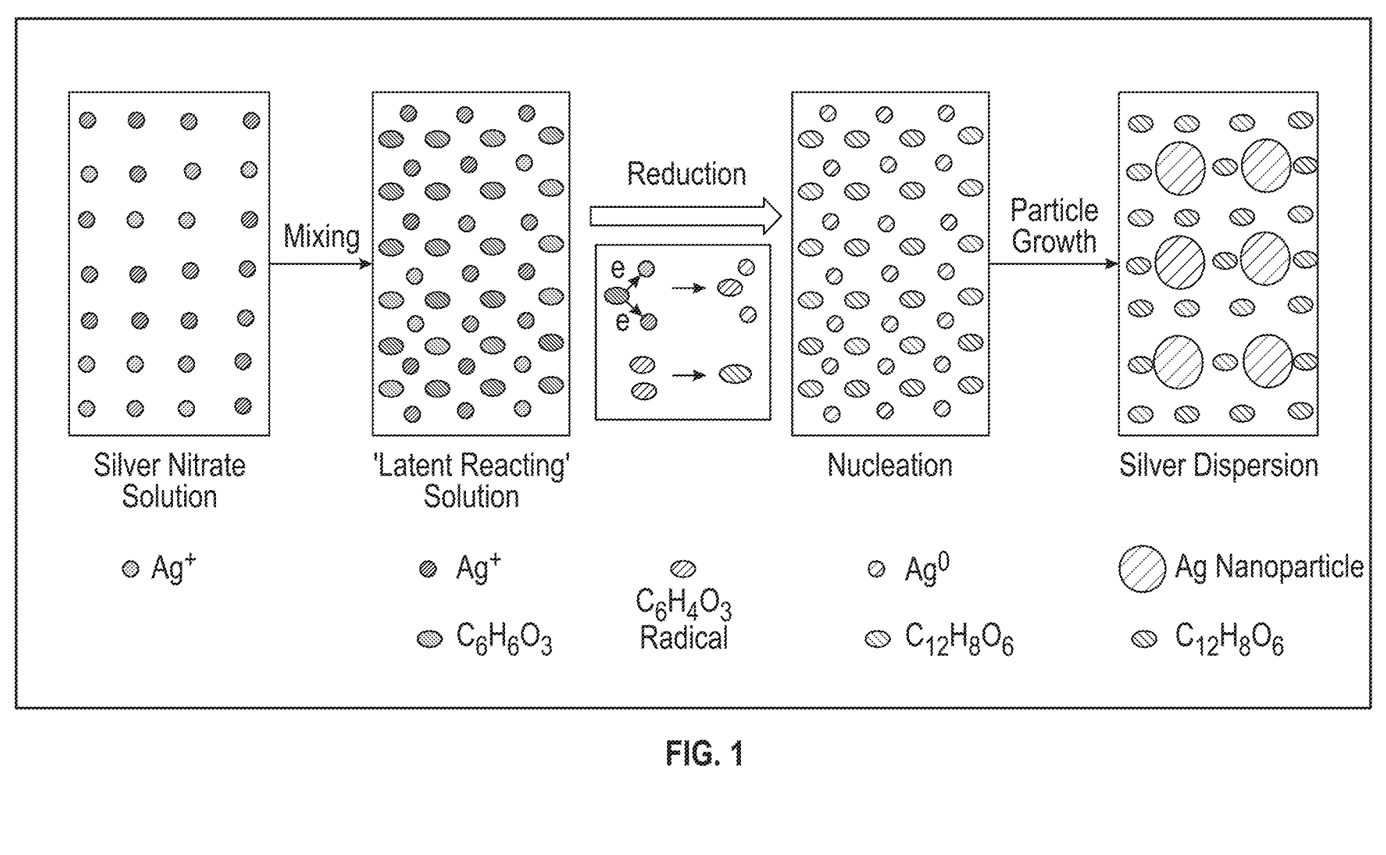
FIG. 1 is a schematic representation of the mechanism of reduction and silver nanoparticles formation as disclosed herein.

The disclosed precipitation process comprises rapidly and uniformly achieving a high pH in the entire reaction volume. For this purpose, the solution containing the silver nitrate and phloroglucinol (the latent reaction mixture) is vigorously agitated prior the addition of sodium hydroxide solution. Next, a concentrated solution of sodium hydroxide is used to minimize the volume of base added. Finally, the base is added rapidly (i.e., dumping, quenching) in the latent reaction mixture (less than 1 second). These steps ensure that the high pH needed for a fast reduction is realized evenly in the reaction space before the electron transfer begins. The sequence of steps is illustrated schematically in FIG. 1.

The disclosed precipitation system generates much smaller silver nanoparticles than those obtained when using resorcinol or hydroquinone despite the later having similar reducing prowess. Without wishing to be bound by theory, the difference can be explained by the unique reduction mechanism of phloroglucinol. In the case of benzenediols (resorcinol and hydroquinone) the oxidation process leads to a stable monomolecular byproduct with roughly the same size and molecular weight (see Eq. 1). In the case of phloroglucinol, however, the oxidation yields first to an unstable monomolecular intermediate radical, which reacts rapidly to form a larger bimolecular entity as confirmed by both electrophoretic and chromatographic studies. (Eq. 2, 3).

$$2C_6H_6O_3 \rightarrow 2C_6H_4O_3 \cdot + 4H^+ + 4e^-$$  Eq. 2

$$2C_6H_4O_3 \cdot \rightarrow C_{12}H_8O_6$$  Eq. 3

The larger molecular weight byproduct is more effective in screening the attractive forces between the silver nanoparticles and preventing their aggregation. As a result, the final size of silver nanoparticles in some aspects does not exceed 10-12 nm. In contrast, the smaller monomolecular byproduct resulting from the oxidation of benzenediols allows the aggregation of the primary crystallites into 40-100 nm spheres in the case of resorcinol and 300-3,000 nm spheres in the case of hydroquinone.

Surprisingly, despite the high silver concentration and elevated ionic strength of the reduction system, the presence of polymeric organic compounds to prevent the aggregation of the silver nanoparticles is not necessary. Without wishing to be bound by theory, a reason for this finding is likely the larger size of the oxidation byproduct of phloroglucinol which is highly effective in preventing the aggregation of the growing primary particles/crystallites of silver. The advantages of the disclosed process for preparing dispersions of silver nanoparticles include uniform size distribution, a small particle size, stable dispersions of the silver nanoparticles, and dispersions with high concentrations of silver nanoparticles. The dispersions can be concentrated to afford even higher concentrations of silver nanoparticles.

Compositions

Described herein, in certain embodiments, are compositions and dispersions comprising silver or silver-based particles.

Disclosed herein are processes of preparing silver nanoparticles with benzene triols such as phloroglucinol, which has been shown to reduce rapidly and completely silver nitrate to metallic (elemental) silver at ambient temperature in aqueous medium.

Without wishing to be bound by theory, the silver nitrate and phloroglucinol form a 'latent reacting mixture' at acidic pH, which allows their homogeneous distribution without electron transfer to occur.

In certain embodiments, a highly alkaline pH (≥13.0) is achieved for a rapid electron transfer between the components of the latent reaction mixture. In certain embodiments, this condition ensures a complete reduction of silver ions to metallic silver and a fast 'nucleation burst' that yields uniform silver nanoparticles.

In certain embodiments, concentrated sodium hydroxide solution (or other base or concentrated base) is rapidly added to the 'latent reaction mixture' to ensure that the pH rises to the target value of >13.0 before the electron transfer between silver and phloroglucinol occurs. In certain embodiments, this results in a fast and uniform nucleation and the formation of very small and uniform silver nanoparticles.

In certain embodiments, intense shear mixing rapidly disperses the base in the 'latent reaction mixture' and establish the highly alkaline conditions before the electron transfer from reductant molecules to silver ions proceeds. The reaction mixture can be agitated vigorously to rapidly disperse the base in the 'latent reaction mixture'. In some aspects, a fast-spinning tree-blade marine propeller can be particularly suitable for this purpose.

In certain embodiments, phloroglucinol generates highly uniform and perfectly dispersed about 10 nm (or between 5-15 nm, or between 8-12 nm, or less than 15 nm) particles at a metal concentration of up to about 2% without the need of dispersing agents.

In certain embodiments, the oxidation of phloroglucinol follows a surprising unique mechanism that generates byproducts of larger molecular weight capable of preventing the aggregation of primary silver particles and the formation of uniform final silver nanoparticles with diameters about 10 nm (or between 5-15 nm, or between 8-12 nm, or less than 15 nm).

In certain embodiments, the silver particles prepared according to the disclosed precipitation process can be maintained indefinitely fully dispersed even after the excess phloroglucinol and its oxidation byproducts are removed by dialysis.

In certain embodiments, stable aqueous dispersions containing up to 60 wt. % silver nanoparticles can be obtained by ultrafiltration without the need for colloid stabilizers.

In an aspect, provided herein is a composition, comprising a dispersion of uniform silver nanoparticles having a diameter of up to about 15 nm. In some embodiments, the nanoparticles have a diameter ranging from about 5 nm to about 15 nm. In some embodiments, the nanoparticles have a diameter ranging from about 9 nm to about 13 nm. In some embodiments, the nanoparticles have a diameter ranging from about 10 nm to about 12 nm. In some embodiments, the nanoparticles have a diameter of about 0.5, about 1.0, about 1.5, about 2.0, about 2.5, about 3.0, about 4.0, about 5.0, about 6.0, about 7.0, about 8.0, about 9.0, about 10, about 11, about 12, about 13, about 14, about 15 nm. In some embodiments, the nanoparticles have a diameter of about 10 nm. In some embodiments, at least 98% of the nanoparticles have a diameter ranging from about 10 nm to about 12 nm. In some embodiments, at least 98% of the nanoparticles have a diameter of about 0.5, about 1.0, about 1.5, about 2.0, about 2.5, about 3.0, about 4.0, about 5.0, about 6.0, about 7.0, about 8.0, about 9.0, about 10, about 11, about 12, about 13, about 14, about 15 nm. In some embodiments, at least 98% of the nanoparticles have a diameter of about 10 nm.

In some embodiments, the dispersion comprises from about 0.1 wt % to about 75 wt % of silver nanoparticles. In some embodiments, the dispersion comprises from about 1 wt % to about 5 wt % of silver nanoparticles. In some embodiments, the dispersion comprises from about 1 wt % to about 3 wt % of silver nanoparticles. In some embodiments, the dispersion is concentrated to comprise up to about 2 wt % of silver nanoparticles.

In some embodiments, the dispersion is concentrated to comprise from about 50 wt % to about 70 wt % of silver nanoparticles. In some embodiments, the dispersion is concentrated to comprise up to about 60 wt % of silver nanoparticles. In some embodiments, the silver is elemental silver.

In some embodiments, the dispersion comprises about 0.1, about 0.2, about 0.3, about 0.4, about 0.5, about 0.6, about 0.7, about 0.8, about 0.9, about 1.0, about 2.0, about 3.0, about 4.0, about 5.0, about 6.0, about 7.0, about 8.0, about 9.0, about 10, about 15, about 20, about 25, about 30, about 35, about 40, about 45, about 50, about 55, about 60, about 65, about 70, or about 75 wt % of silver nanoparticles.

In some embodiments, the composition is stable for a period of at least about 12 months.

In some embodiments, the silver nanoparticles are free of coatings. In some embodiments, the silver nanoparticles are free of organic coatings.

In another aspect, provided herein is a composition, comprising a homogeneous solution of silver nitrate and a benzene triol. In some embodiments, the benzene triol is phloroglucinol.

In some embodiments, the composition further comprises at least one oxidation product of the benzene triol.

In some embodiments, the benzene triol is phloroglucinol. In some embodiments, the composition is acidic.

In some aspects, a composition is provided, comprising a dispersion of uniform silver nanoparticles having a diameter of up to about 15 nm. The nanoparticles have a diameter ranging from about 5 nm to about 15 nm. The nanoparticles can have a diameter ranging from about 9 nm to about 13 nm. The nanoparticles can have a diameter ranging from about 10 nm to about 12 nm. The dispersion can comprise from about 1 wt % to about 5 wt % of silver nanoparticles. The dispersion can be concentrated to comprise up to about 60 wt % of silver nanoparticles. The silver can comprise elemental silver.

In some aspects, a composition comprising a homogeneous solution of silver nitrate and a benzene triol is provided. The composition can further comprise at least one oxidation product of the benzene triol. In some aspects, the benzene triol can be phloroglucinol. In some aspects, the composition can be acidic. In some aspects, the composition can be stable for a period of about 12 months. In some aspects, the silver nanoparticles are free of polymeric coatings.

In some aspects, an inkjet printing formulation is provided, comprising the silver nanoparticles of the compositions and methods described herein In another aspect, the dried inkjet printed deposits are electrically conductive at room temperature.

In some aspects, a drug delivery vector is provided, comprising the silver nanoparticles of the compositions and methods described herein. In some aspects, the vector further comprises at least one therapeutic agent. In some aspects, the vector comprises a therapeutically effective amount of at least one therapeutic agent.

Processes

In an aspect, provided herein is a process of preparing a composition comprising a dispersion of uniform silver nanoparticles, comprising contacting or reacting silver nitrate with a benzene triol at about 25° C. in the presence of a solvent to afford a homogeneous latent reaction mixture of benzene triol and silver ions.

In some embodiments, the solvent is water.

In some embodiments, the solvent is a water and alcohol mixture where the alcohol is completely miscible with water. The alcohol may be a low molecular weight aliphatic one such as methanol, ethanol, propanol and its isomers.

In some embodiments, the benzene triol is phloroglucinol.

In some embodiments, the process further comprises monitoring the pH.

In some embodiments, process is conducted under neutral or acidic conditions.

In some embodiments, the latent reaction mixture comprising a solution of silver nitrate and a benzene triol is vigorously agitated.

In some embodiments, the reaction is quenched by the rapid addition of concentrated base to the reaction mixture.

In some embodiments, the base is an alkali hydroxide. In some embodiments, the base is sodium hydroxide. In some embodiments, the base is potassium hydroxide.

In some embodiments, base is added until a pH of at least 11, at least 12, at least 13, or about 13 or greater is achieved. In some embodiments, the reaction has a pH of about 13.0, about 13.1, about 13.2, about 13.3, about 13.4, about 13.5, about 13.6, about 13.7, about 13.8, about 13.9, or about 14 upon quenching with base.

In some embodiments, the quenching is achieved by adding concentrated base to the reaction mixture over a period of up to about 5 seconds.

In some embodiments, the quenching is achieved by adding concentrated base to the reaction mixture over a period of up to about 2 seconds. In some embodiments, the quenching is achieved by adding concentrated base to the reaction mixture over a period about 0.5, about 1, about 1.5, about 2, about 2.5, about 3, about 3.5, about 4, about 4.5, or about 5 seconds. In some embodiments, the quenching is achieved by adding concentrated base to the reaction mixture over a period about 1, second. In some embodiments, the quenching is achieved by adding concentrated base to the reaction mixture over a period of up to 1 second, up to 2 seconds, up to 3 seconds, up to 4 seconds, or up to 5 seconds.

In some embodiments, the concentration of the sodium hydroxide is about 1N. In some embodiments, the concentration of the sodium hydroxide is about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10N sodium hydroxide. In some embodiments, the concentration of the sodium hydroxide is between 0.1-10N, between 1-10N, between 0.1-2N, between 0.5-3N, or between 0.1-5N.

In some embodiments, a bimolecular byproduct of phloroglucinol is formed.

In some embodiments, the aggregation of silver particles is prevented.

In some embodiments, the process does not comprise addition of an organic polymer.

In some embodiments, the process further comprises removing excess phloroglucinol and its oxidation byproducts by dialysis.

In some embodiments, the process further comprises the step of separating the silver particles from the mixture and optionally the step of drying the particles.

In some embodiments, the silver particles are separated by ultrafiltration.

In some embodiments, the process does not comprise the addition of a colloid stabilizer. In some embodiments, the silver nanoparticles are free of a colloid stabilizer. In some embodiments, the reaction mixture is free of a colloid stabilizer.

In some embodiments, the process is conducted in the absence of a dispersing agent. In some embodiments, the process does not comprise the thermal decomposition of silver(+1)-oxide species. In some embodiments, the process does not require heat. In some embodiments, the latent reaction mixture is free of a dispersing agent. In some embodiments, the process is carried out in the absence of polysaccharides.

In some aspects, a process of preparing a composition comprising a dispersion of uniform silver nanoparticles is provided, comprising contacting or reacting silver nitrate with a benzene triol at about 25° C. in the presence of a solvent to afford a homogeneous latent reaction mixture of benzene triol and silver ions. The solvent can comprise at least one of water and alcohol miscible with water. The benzene triol can be phloroglucinol. The process can comprise a step of monitoring the pH. Additionally or alternatively, the process can be conducted under neutral or acidic conditions. Additionally or alternatively, the latent reaction mixture comprising a solution of silver nitrate and a benzene triol (after the step of contacting or reacting) can be vigorously agitated. Additionally or alternatively, the reaction can be quenched by the rapid addition of concentrated base to the reaction mixture. The base can comprise sodium hydroxide. The concentration of the sodium hydroxide is between 0.5N and 10N. Additionally or alternatively, the base can be added until a pH of about 13 or greater is achieved. Additionally or alternatively, the quenching can be achieved by adding concentrated base to the reaction mixture over a period of up to about 5 seconds, or up to about 1 second. In some aspects of the processes described herein, a bimolecular byproduct of phloroglucinol can be formed. In some aspects of the processes described herein, the aggregation of silver particles can be prevented. In some embodiments of the processes described herein, the process does not comprise addition of an organic polymer. Additionally or alternatively, the process can comprise removing excess phloroglucinol and its oxidation byproducts by dialysis. Additionally or alternatively, the process can comprise the step of separating the silver particles from the mixture and optionally the step of drying the particles. The silver particles can be separated by ultrafiltration, and the process can lack the addition of a colloid stabilizer.

EXAMPLES

Figure 4:
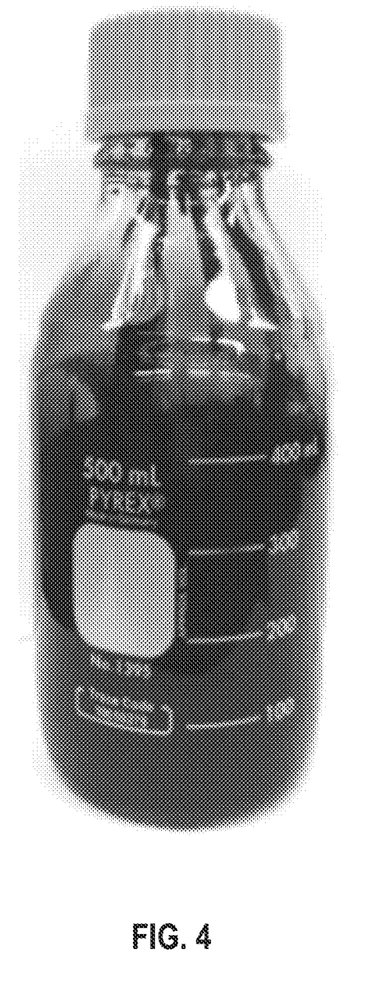
FIG. 4 is an image of an indefinitely stable aqueous dispersion containing 60 wt. % silver as 10 nm nanoparticles.

Example 1. Synthesis of Silver Nanoparticles 880 ml DI H2O are introduced into a 1.5 L glass beaker. After adjusting the temperature to 25° C., 14.0 g phloroglucinol dihydrate are dissolved under mixing. Next, a solution obtained by dissolving 31.5 g AgNO$_3$ (20.0 g Ag metal) in 20 mL DI H$_2$O is added to the phloroglucinol solution. After 5 minutes, 100 mL 1N NaOH solution is added rapidly (dumping) into the AgNO$_3$/phloroglucinol solution. The reduction of silver proceeds within seconds and leads to the formation of a dark brown dispersion (FIG. 4). The dispersion is dialyzed until the conductivity reaches 30 μS to obtain a stable dispersion containing 2 wt. % (0.2 mol·dm$^{-3}$) silver nanoparticles. As needed, this dispersion can be concentrated by ultrafiltration to obtain highly stable dispersions with a silver concentration as high as 60% Ag (600,000 ppm, or 6.0 mol·dm$^{-3}$).

V. Particles Characterization

Figure 2:
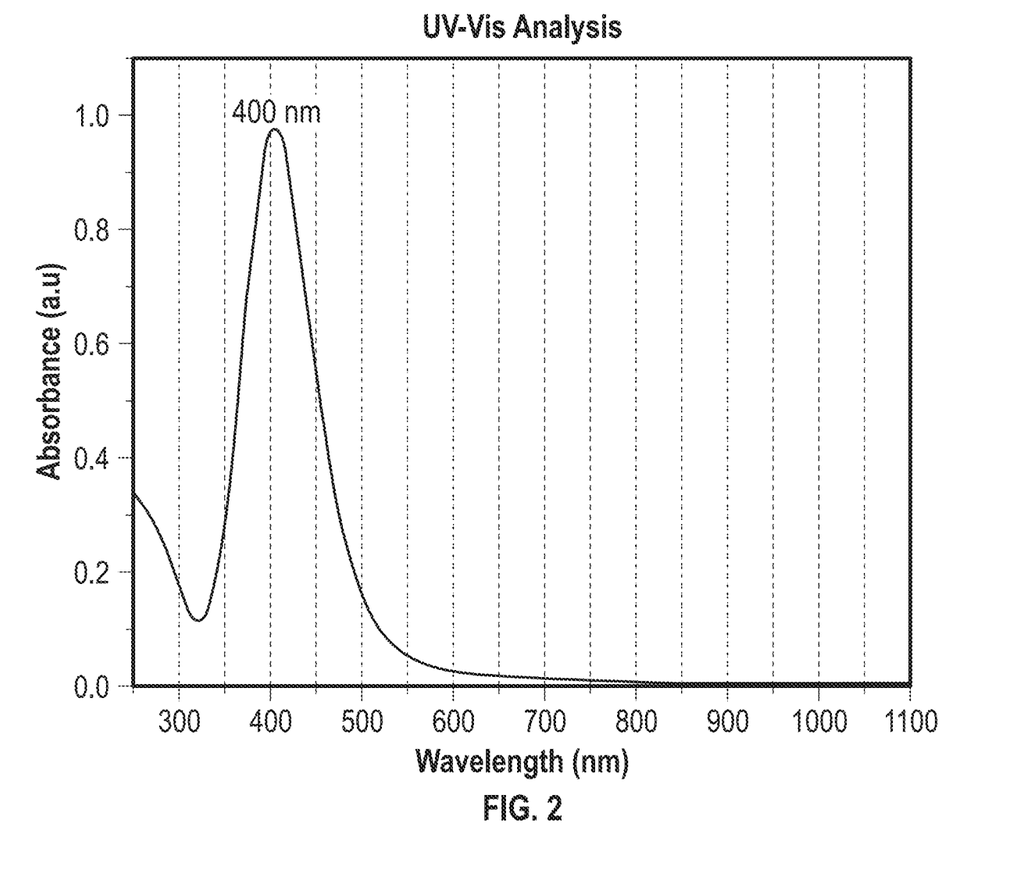
FIG. 2 shows UV-Vis spectrum of the 2 wt % Ag raw dispersion diluted 100 times.

The UV-Vis spectrum of the dialyzed dispersion diluted 100× is shown in FIG. 2. The very narrow plasmon band at 400 nm suggests the presence of highly uniform nanoparticles while the lack of background absorption over 600 nm indicates the absence of large silver entities (individual particles or aggregates). The stability of the dispersion was excellent as indicated by the lack of particles settling or change in the UV-Vis spectrum after 12 months. FIGS.

Figure 3A:
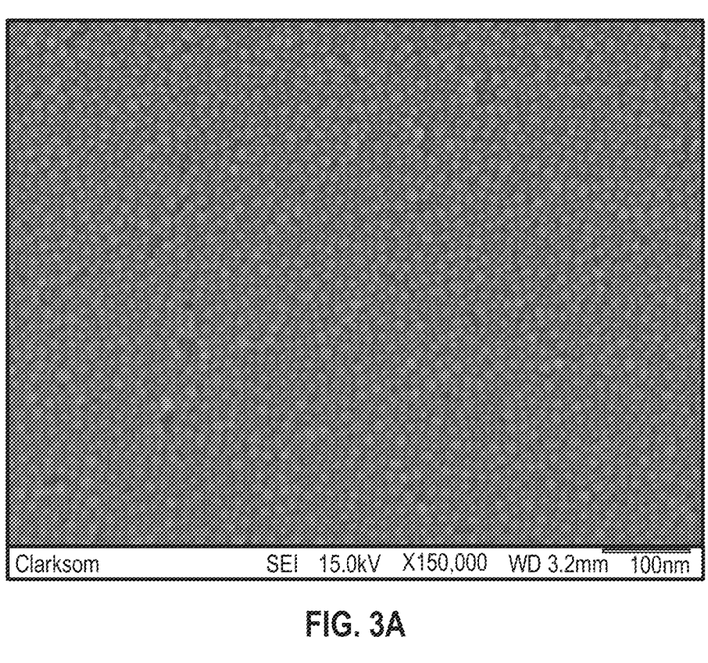
FIGS. 3A-3B show the FESEM (3A) and STEM (3B) images of Ag nanoparticles prepared in Experiment 1.
Figure 3B:
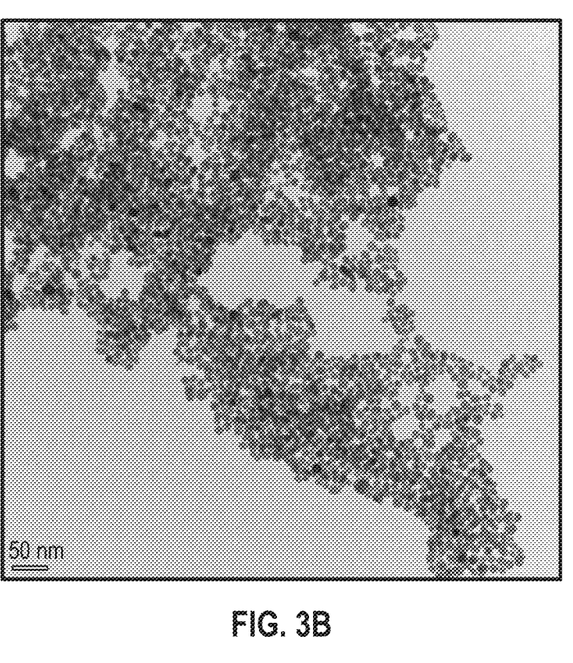

3A-3B show the FESEM (3A) and STEM (3B) images, which demonstrate the presence of uniform nanoparticles with an average size of about 10 nm and confirmed the absence of larger particles or aggregates.

The dialyzed dispersion can be further concentrated by, for example, ultrafiltration to form an indefinitely stable dispersion containing about 60 wt % silver nanoparticles. The concentrated dispersion can be considered in final form for inkjet printing formulations in electronics applications or can be used in diluted form for antimicrobial and optoelectronic purposes. The silver nanoparticles can be also functionalized for optimum biocompatibility and bioavailability when used as vector in drug delivery and other bio-medical applications.

It should be appreciated that modifications to Example 1 are contemplated herein. For example, it is contemplated that the temperature can be adjusted to between 20-30° C. or any suitable temperature prior to dissolving phloroglucinol dihydrate in water or other solvent. It is contemplated that about 1 g phloroglucinol dihydrate can be dissolved per about 55-70 ml deionized water or other solvent, or any suitable amount. It is contemplated that about 1 g of Ag metal can be dissolved in between 0.5-1.5 mL of deionized water or other solvent, or any suitable amount, prior to adding the resulting solution to the phloroglucinol solution. It is contemplated any suitable amount of a base (e.g., a concentrated base) can be rapidly added (e.g., within about 1 second, within about 2 seconds) to the combined phloroglucinol solution/silver solution. For example, it is contemplated that 100 mL of a concentrated base can be rapidly added to 700-1100 mL of the combined phloroglucinol solution/silver solution.

Thus, specific examples of silver nanoparticle dispersions, compositions, vectors and formulations, and methods of preparing such compositions, dispersions, vectors and formulations have been disclosed. It should be apparent, however, to those skilled in the art that many more modifications besides those already described are possible without departing from the inventive concepts herein. While examples and variations of the many aspects of the invention have been disclosed and described herein, such disclosure is provided for purposes of explanation and illustration only. Thus, various changes and modifications may be made without departing from the scope of the claims.

The terminology used herein is for the purpose of describing particular cases only and is not intended to be limiting. The below terms are discussed to illustrate meanings of the terms as used in this specification, in addition to the understanding of these terms by those of skill in the art. As used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An "effective amount" for non-therapeutic uses (e.g., a sanitizer/disinfectant for an inanimate surface) is the amount of the composition including a compound as disclosed herein required to provide a clinically significant decrease in microbial growth or microbial inhibition. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

Reference throughout this specification to "an embodiment" or "an implementation" means that a particular feature, structure, or characteristic described in connection with the embodiment is included in at least one embodiment or implementation. Thus, appearances of the phrases "in an embodiment" in various places throughout this specification are not necessarily all referring to the same embodiment or a single exclusive embodiment. Furthermore, the particular features, structures, or characteristics described herein may be combined in any suitable manner in one or more embodiments or one or more implementations.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

All structural and functional equivalents to the components of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

Although the disclosure has been described with reference to the above examples, it will be understood that modifications and variations are encompassed within the spirit and scope of the disclosure. Accordingly, the disclosure is limited only by the following claims.

What is claimed is:

1. A method of preparing a composition comprising a dispersion of silver nanoparticles, comprising: contacting silver nitrate with phloroglucinol at between 20-30 degrees Celsius in the presence of a solvent to form a homogenous mixture free of a dispersing agent;

and quenching the homogenous mixture by the addition of a base to the homogenous mixture, wherein the base is added to the homogenous mixture until a pH of at least 11 is achieved, and wherein the addition of the base to the homogenous mixture takes no more than 5 seconds.

2. The method of claim 1, wherein the solvent is at least one of water and an alcohol miscible with water.

3. The method of claim 1, wherein the contacting occurs in neutral or acidic conditions.

4. The method of claim 1, further comprising: agitating the homogenous mixture after the step of contacting and prior to the quenching; and removing excess phloroglucinol and its oxidation byproducts from the quenched mixture by dialysis.

5. The method of claim 1 wherein the addition of the base to the homogenous mixture takes no more than 1 second.

6. The method of claim 1 wherein the base is added to the homogenous mixture until a pH of about 13 is achieved.

* * * * *